(12) United States Patent
Skinner

(10) Patent No.: US 7,270,540 B2
(45) Date of Patent: *Sep. 18, 2007

(54) ADJUSTABLE DENTAL IMPRESSION TRAY AND METHODS FOR USING SAME

(76) Inventor: Gregory C. Skinner, 250 S. Lyon Ave., Suite B, Hemet, CA (US) 92543

( * ) Notice: Subject to any disclaimer, the term of this patent is extended or adjusted under 35 U.S.C. 154(b) by 193 days.

This patent is subject to a terminal disclaimer.

(21) Appl. No.: 10/427,733

(22) Filed: May 1, 2003

(65) Prior Publication Data

US 2004/0009451 A1 Jan. 15, 2004

Related U.S. Application Data

(63) Continuation-in-part of application No. 09/649,198, filed on Aug. 28, 2000, now Pat. No. 6,629,841.

(51) Int. Cl.
*A61C 9/00* (2006.01)
(52) U.S. Cl. ........................................................ 433/43
(58) Field of Classification Search ............... 433/41, 433/42, 44, 45, 37, 214, 72, 73, 74, 76; 33/513, 33/514
See application file for complete search history.

(56) References Cited

U.S. PATENT DOCUMENTS

| | | | | |
|---|---|---|---|---|
| 257,038 | A * | 4/1882 | McMann | 433/41 |
| 2,594,832 | A | 4/1952 | Wentzel | 433/41 |
| 2,685,137 | A | 8/1954 | Thompson | 433/41 |
| 2,860,414 | A | 11/1958 | Brant | 433/43 |
| 3,574,259 | A | 4/1971 | Jones | 433/43 |
| 3,878,610 | A * | 4/1975 | Coscina | 433/37 |
| 3,987,548 | A | 10/1976 | Jones | 433/43 |
| 4,145,812 | A | 3/1979 | Johnson et al. | 32/17 |

(Continued)

FOREIGN PATENT DOCUMENTS

FR 737739 12/1932 ................. 433/43

(Continued)

*Primary Examiner*—Todd E. Manahan
(74) *Attorney, Agent, or Firm*—Pate Pierce & Baird

(57) ABSTRACT

An adjustable dental impression tray including a first arcuate member and a second arcuate member configured to selectively engage the first arcuate member. The first and second arcuate members forming a channel adapted to receive a quantity of impression material. The adjustable dental impression tray having a handle formed at one end which facilitates the introduction and removal of the impression tray into and from the mouth of a patient. An adjustment mechanism engageably disposed in relation to the first and second arcuate members, wherein the adjustment mechanism provides for the selective adjustment of the first arcuate member in at least one fixed position relative to the second arcuate position, wherein defining one or more widths of the channel. Preferably, the channel is formed having a general U-shaped configuration which approximates the various sizes of the dentition of a patient. In preferred design, each of the arcuate members comprise an outer wall, an inner wall and a platform surface. A locking member is preferably formed in relation to the arcuate members to receive and retain the impression material in relation to the channel. In addition, one or more notches may be formed in the length of the arcuate members to provide means for removing at least a portion of the length of one or both of the arcuate members, thereby forming a "quadrant" or an "anterior" dental tray.

21 Claims, 12 Drawing Sheets

U.S. PATENT DOCUMENTS

| | | | |
|---|---|---|---|
| 4,432,728 A | 2/1984 | Skarky | 433/37 |
| 4,763,791 A | 8/1988 | Halverson et al. | 206/570 |
| 5,040,976 A | 8/1991 | Ubel, III et al. | 433/41 |
| 5,064,371 A | 11/1991 | Smeltzer | 433/37 |
| 5,076,785 A | 12/1991 | Tsai | 433/46 |
| 5,297,960 A | 3/1994 | Burns | 433/41 |
| 5,336,086 A | 8/1994 | Simmen et al. | 433/37 |
| 5,340,308 A | 8/1994 | Cukjati | 433/41 |
| 5,503,497 A | 4/1996 | Dudley et al. | 403/103 |
| 5,513,985 A | 5/1996 | Robertson | 433/38 |
| 5,580,244 A | 12/1996 | White | 433/37 |
| 5,582,488 A | 12/1996 | Dudley et al. | 403/103 |
| 5,636,985 A | 6/1997 | Simmen et al. | 433/37 |
| 5,733,118 A | 3/1998 | Pankuch et al. | 433/38 |
| 6,071,121 A | 6/2000 | Simon | 433/37 |
| 6,428,315 B1 | 8/2002 | Prestipino et al. | 433/45 |

FOREIGN PATENT DOCUMENTS

| | | | |
|---|---|---|---|
| FR | 2551654 A1 * | 3/1985 | |
| FR | 2606271 A * | 5/1988 | |
| IT | 417420 | 1/1947 | 433/33 |

* cited by examiner

ADJUSTABLE DENTAL IMPRESSION TRAY AND METHODS FOR USING SAME

RELATED APPLICATIONS

This application is a continuation-in-part of my patent application Ser. No. 09/649,198, filed Aug. 28, 2000 now U.S. Pat. No. 6,629,841 and entitled "ADJUSTABLE DENTAL IMPRESSION TRAY AND METHODS FOR USING SAME," and incorporated herein by reference.

BACKGROUND

1. Field of the Invention

This invention relates to dental implements and, more particularly, to novel dental impression trays that are mechanically adjustable to accommodate various mouth sizes in order to obtain an accurate impression of an upper and/or lower dentition of a patient.

2. The Background Art

With regards to dentistry, an impression is often used to create an imprint or negative likeness of the teeth and adjacent portions of the jaw (e.g., tooth formations, the contour of the gums, etc.) preparatory to dental repair, orthodontics and restoration of missing dental structures. Impressions are typically made by placing a soft, semi-fluid material within the confines of an open trough or channel of a unitary arcuate tray which is then positioned within the mouth of a patient, thus allowing the material to set or cure. Depending upon the material used, the set impression may be either hard or have some elastic characteristics.

To provide the most accurate articulation, the impression cast should generally represent the entire dental arch. In this regard, the impression cast can be used to establish interproximal contacts, buccal and lingual contours and occlusion with the opposing teeth. From the negative or female cast of the teeth and surrounding structures, a positive reproduction or male cast may be created for the purpose of fabricating inlays, crowns, bridge retainers, dentures, restorations or the like.

Traditionally, before an impression cast of the dentition is created, a stock tray is selected by the dentist or dental assistant that will generally fit the dental arch of the particular patient. Since the dental arch may differ widely from patient to patient, various sizes of impression trays (e.g., small, medium, large and extra large) were developed by those skilled in the art to accommodate various mouth sizes, bite radii of teeth and to correspond to the upper and lower anterior or quadrant impression sites of patients.

For example, those skilled in the art developed prior art dental impression trays that are formed of metal, such as stainless steel, and have a pair of spaced-apart vertical walls joined by a semi-rigid mesh material disposed horizontally between the opposing vertical walls. Extending outwardly in structural relation to at least a portion of the surface facing of one of the vertical walls, a handle member may be provided to facilitate a means for gripping the impression tray for the purpose of facilitating manual manipulation of the tray. In addition, an open trough or channel may generally be formed between the opposing vertical walls, wherein the horizontally disposed mesh material provides a porous surface flooring for the trough. In preferred operation, the mesh material provides a means for permitting excess flow of impression material to become displaced and extruded there through. Dental impression trays of the prior art may further include openings formed in the vertical walls of the trough or channel which generally function as an anchoring surface for the impression, thus allowing the excess flow of impression material to become attached thereto.

Although seemingly useful for their intended purposes, there are several practical disadvantages of the prior art dental impression trays that are comprised of metal. For example, a significant disadvantage of prior art metal impression trays includes the difficulty associated with maintaining proper cleaning and sanitation of the impression trays using heat and/or chemical sterilization methods or techniques in an effort to avoid cross-contamination from one patient to another and in order to reuse these various sized, stock metal impression trays from patient to patient.

Attempting to alleviate some of the disadvantages associated with the amount of time and energy expended to maintain proper sanitation and sterilization of prior art metal impression trays, in addition to the significant costs associated therewith, disposable impression trays were developed by those skilled in the art. As noted above, since a dental arch may differ widely from patient to patient, various sizes of disposable impression trays (e.g., small, medium, large and extra large) were developed by those skilled in the art to accommodate various mouth sizes, bite radii of teeth and to correspond to the upper and lower anterior or quadrant impression sites of patients.

In accordance with other such prior art apparatus and techniques for making an impression cast of the upper and/or lower dentition of a patient, those skilled in the art developed adjustable impression trays. For example, an adjustable impression tray of the prior art may comprise a primary impression unit and a movable extension unit telescopically mounted on the primary unit for adjustment relative thereto. The primary unit may be provided with primary leg portions having secondary leg portions extending therefrom, wherein the primary leg portions include a first flap means extending outwardly therefrom and over the secondary leg portions. In operation, the secondary leg portions comprise a tab means that cooperates with the first flap means of the primary leg portions so as to facilitate the first flap means being movable relative to the tab means. The movable extension unit may further include a second flap means having a series of slots formed therein for registry with the tab means of the secondary leg portions to facilitate selective fixation in relation to the primary leg portions of the impression tray.

Another example of prior art adjustable impression trays includes a main arcuate portion with parallel spaced vertical walls having extension portions slidably disposed in frictional engagement for lengthwise adjustment in relation to the main arcuate portion. The engagement means between the extension portions and the main arcuate portion of the impression tray may include T-shaped rails formed in the outer faces of the opposing walls and corresponding recesses formed in the inner faces of the respective walls of the extension portions. Similarly, annular recesses may be formed in the outer faces of the opposing walls and corresponding annular ribs may be formed in the inner faces of the respective walls of the extension portions to provide a slidable engagement therebetween.

A meaningful disadvantage with prior art adjustable impression trays of the general type discussed herein is that they seem to only provide means for accommodating a structural adjustment in the dimensional length of the channel. In this regard, because these prior art adjustable impression trays fail to provide for any adjustment in the dimensional width of the tray to accommodate various sizes of the dental arch of patients, they are generally limited in their particular utilization.

In an effort to accommodate an adjustment in the dimensional width of a dental impression tray, those skilled in the art developed heat-expansive impression trays which may be formed of a thermoplastic material that becomes malleable at elevated temperatures so that the impression tray can be generally shaped and configured in such a manner so as to accommodate a corresponding dental arch of a particular patient. For example, prior art heat-expansive impression trays may structurally comprise an elongated channel including a buccal side, a lingual side and an occlusal side. The occlusal side of the channel including an outwardly extending folded section which may be fully or partially unfolded when the channel is heated, thereby providing a means for expanding the dimensional width of the elongated channel. Two additional folded sections formed in opposed posterior portions of the impression tray may also be provided which, when heated at a specific "softening" temperature, can be partially or fully unfolded by pulling the posterior ends of the tray away from the anterior portion of the same, thus extending the dimensional length of the elongated channel.

While prior art adjustable and heat-expansive impression trays may appear generally suitable for their intended purposes, these impression trays of the prior art nevertheless leave much to be desired from the standpoint of effectiveness of operation, manufacturing costs, simplicity of construction in relation to multiplicity of parts, and functionality as to universal application. As will be appreciated in this particular art, economic considerations are significant when dealing with the highly competitive dental industry, since multiple stock impression trays (e.g., small, medium, large and extra large) or complicated, multifaceted devices are frequently found to be commercially impractical. Accordingly, even a slight savings in cost may substantially enhance the commercial appeal of a particular component or assembly when considering issues of mass production of the product.

In accordance therewith, it would be desirable to provide an adjustable dental impression tray which realizes the advantages of the prior art devices while at the same time eliminates the disadvantages associated therewith. Such an adjustable dental impression tray is disclosed and claimed herein.

BRIEF SUMMARY AND OBJECTS OF THE INVENTION

In view of the foregoing, it is a primary object of the present invention to provide novel dental impression trays which may be mechanically adjusted to accommodate various mouth sizes, bite radii of teeth and to correspond to the upper, lower, anterior, quadrant or triple bite impression sites.

It is also an object of the present invention to provide an adjustable dental impression tray which is formed of a disposable material, thus avoiding the disadvantages associated with having to sanitize and sterilize metal impression trays.

It is further an object of the present invention to provide an adjustable dental impression tray which may be adjusted to the specific size of a patient's mouth, thereby eliminating the need for a dentist to stock various sizes of impression trays (e.g., small, medium, large and extra large) in order to accommodate the different dental arch configurations of patients.

Additionally, it is an object of the present invention to provide an adjustable dental impression tray which increases the accuracy of the impression cast, while decreasing dental chair time.

Similarly, it is an object of the present invention to provide an adjustable dental impression tray which reduces the possibility of deformation of the impression cast.

It is a still further object of the present invention to provide an adjustable dental impression tray which is simple in construction, effective in operation and inexpensive to manufacture.

Consistent with the foregoing objects, and in accordance with the invention as embodied and broadly described herein, an adjustable dental impression tray includes a first arcuate member having a distal end and a proximal end. A second arcuate member having a distal end and a proximal end which is preferably movably connected to the first arcuate member adjacent the proximal end of each of the arcuate members. Each arcuate member is configured to receive a quantity of impression material in relation thereto. A handle may also be attached to one or both of the arcuate members to facilitate easy removal of the dental impression tray from a patient's mouth with minimal deformation of the impression material.

The adjustable dental impression tray of the present invention preferably includes an adjustment mechanism for selectively adjusting the position of the first arcuate member relative to the second arcuate member. The adjustment mechanism may include an opening formed in the first arcuate member, and a second arcuate member having a fastener member corresponding to the opening formed in the first arcuate member. In one presently preferred embodiment of the present invention, the fastener member may include a post or shaft configured within the proximal end of the first arcuate member with the opening positioned within the proximal end of the second arcuate member. The post or shaft and the opening may be correspondingly configured for movable mating engagement with each other, thereby permitting the first and second arcuate members to be selectively positioned relative to each other. In an alternate presently preferred embodiment, the adjustment mechanism may include concentric gears with a spring-loaded button device for releasing the gears and allowing the first and second arcuate members to move relative to each other. When the biased button is disengaged, the concentric gears preferably realign thereby preventing further movement between the arcuate members. Thus, the dental impression tray of the present invention may be pivotally adjustable through a range of motion allowing one dental impression tray to closely and comfortably fit a wide variety of dentition sizes of patients.

In structural design, the first and second arcuate members include an outer wall, respectively. In one presently preferred embodiment of the present invention, the first and second arcuate members each include a frame member attached to and spread apart from the outer wall. Preferably, a membrane may extend between the frame member and a centerline portion of the outer wall of each arcuate member, along the length of the outer wall, thus providing a surface upon which the impression material may be placed. Thus, an upper and lower tray portion may be simultaneously created within the adjustable dental impression tray which allows a mold to be taken of the upper and lower dentition simultaneously. This "triple bite" configuration allows the user to not only create an impression of the upper and lower dentition, but allows the user to create a mold which shows the bite relationship between the two.

The first and second arcuate members are preferably formed such that a portion of the first arcuate member may be positioned to closely overlap a portion of the second arcuate member, thus forming an overlap portion. The first and second arcuate members may be configured such that the first and second arcuate members may be positioned relative to each other to form a substantially U-shaped channel between the outer walls of the first and second arcuate members and a perimeter of the overlap portion. This channel defined by the outer walls of the first and second arcuate members may be configured to approximate the curvature of a person's dentition.

In another presently preferred embodiment of the present invention, the first and second arcuate members may include an inner wall spaced apart from the outer wall which, together with the membrane extending therebetween, form a generally U-shaped channel configured to approximate the curvature of a person's dentition.

The outer wall of at least one of the arcuate members may include one or more notches formed at the proximal end of the arcuate member which permits the user to break the length of the arcuate member at the specified notch. As appreciated, this notch formed at the proximal end of one or both of the arcuate members allows the user to create a "quadrant" dental impression tray for taking an impression of the upper or lower, left or right portions of the patient's dentition, by breaking off the appropriate arcuate member at the specified notch. The outer wall of the arcuate members may also include one or more notches positioned along the length of one or both of the arcuate members between the distal and proximal ends thereof. This notch allows the user to break the length of the respective arcuate member to create an "anterior" dental impression tray for taking a dental impression of the front portion of the upper or lower dentition of a patient.

In another presently preferred embodiment, at lease one of the arcuate members includes a locking member for retaining the impression material. The locking member may include a flange member which extends along at least a portion of one of the arcuate members. In another presently preferred embodiment, the locking member may include receiving apertures or vents configured within the outer wall, inner wall, platform surface or any combinations thereof in relation to at least one of the arcuate members which allows a portion of the impression material to flow through the receiving apertures or vents and anchor itself to arcuate member.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DESCRIPTIONS OF THE PREFERRED EMBODIMENTS

It will be readily understood that the components of the present invention, as generally described and illustrated in the Figures herein, could be arranged and designed in a wide variety of different configurations. Thus, the following more detailed description of the embodiments of the system and method of the present invention, as represented in FIGS. 1 through 19, is not intended to limit the scope of the invention, as claimed, but it is merely representative of the presently preferred embodiments of the invention. The presently preferred embodiments of the invention will be best understood by reference to the drawings, wherein like parts are designated by like numerals throughout.

Figure 1:
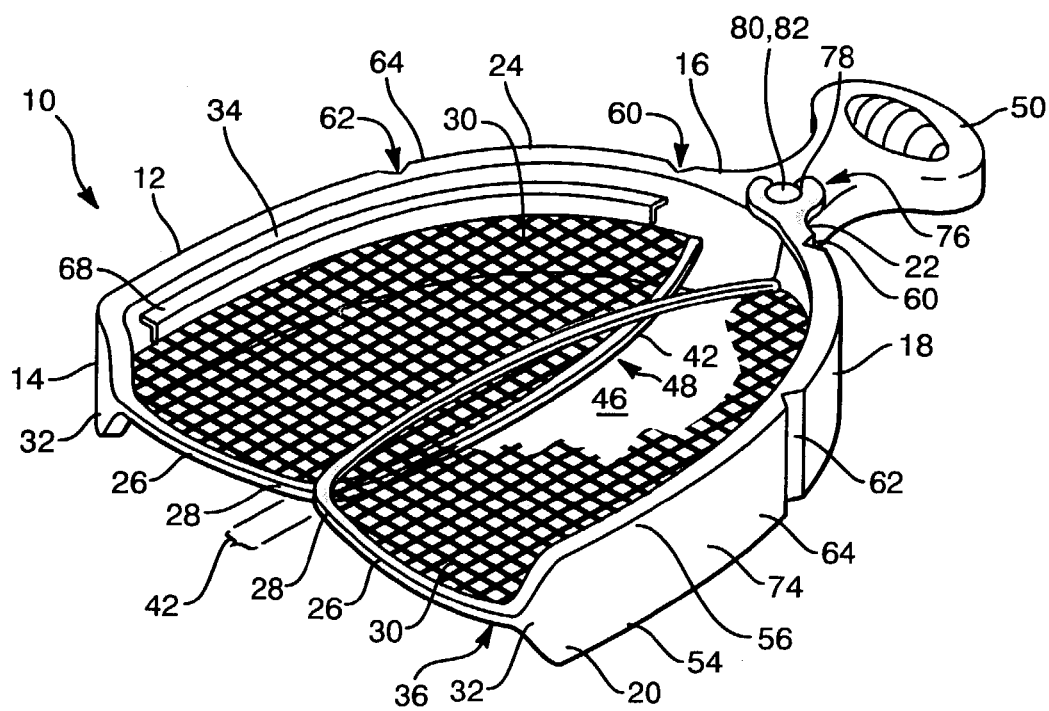
FIG. 1 is a perspective view of one presently preferred embodiment of an adjustable dental impression tray.

One presently preferred embodiment of the present invention, designated generally at 10, is best illustrated in FIG. 1. As shown, an adjustable dental impression tray 10 includes a first arcuate member 12 having a distal end 14 and a proximal end 16. A second arcuate member 18, having a distal end 20 and a proximal end 22, is preferably movably connected to the first arcuate member 12 adjacent the proximal ends 16, 24 of each arcuate member 12, 18, separately. The first and second arcuate members 12, 18 each include an outer wall 24. In one presently preferred embodiment, the first and second arcuate members 12, 18 each include a frame member 26 attached to the outer wall 24. A leading portion 28 of each of the frame members 26 is spaced apart from the outer wall 24 of each of the arcuate members 12, 18. A membrane 30 may extend between the frame member 26 and the outer wall 24 of each arcuate member 12, 18 along the length of the outer wall 24. In this configuration, the arcuate members 12, 18 are suitable for holding an impression material.

Figure 2:
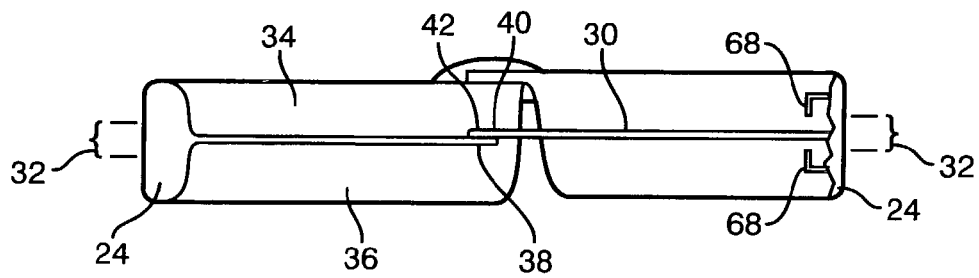
FIG. 2 is a front plan view of the embodiment of FIG. 1 in a partially closed position.

With reference now to FIGS. 1 and 2, the membrane 30, in one presently preferred embodiment of the present invention, extends from a centerline portion 32 of the outer wall 24, preferably along the length of the outer wall 24. It will be appreciated by those skilled in the art that with the membrane 30 extending from the centerline portion 32 of the outer wall 24, an upper 34 and lower 36 tray portion of the adjustable dental impression tray 10 are simultaneously created. It will further be appreciated by those skilled in the art that this creates a "triple bite" or "multiple impression" tray known in the art to allow a mold to be taken of the upper and lower dentition simultaneously in an effort to more accurately determine the relative positions of the upper and lower teeth during a bite. The upper impression corresponds to an impression section of maxilla, the lower impression corresponds to a complimentary section of mandible and the two complimentary impressions jointly provide an impression of the bite relationship of mandible to maxilla.

One suitable material for the membrane 30 is a fabric made from nonwoven spun-bonded filaments. It will be appreciated by those skilled in the art that the weight-to-area ratio of the membrane extending between the outer wall 24 and the frame member 26, and the air permeability between the upper 34 and lower 36 tray portions may be predetermined for maximum advantage. In one embodiment, the weight-to-area ratio may be less than 0.4 ounces per sheet yard as the membrane extends between the outer wall 24 and the frame member 26. The air permeability, in one presently preferred embodiment, may be greater than about 110 cubic feet per minute per square foot as measured according to ASTM-D.737-75 standards. Other examples of the materials forming the membrane 30 may include, by way of illustration and not by limitation, perforated or continuous sheets of silicone-based film, foil or other highly malleable metal, either continuous or perforated, ceramics, plastics, rubbers, composite materials or other metals or metal alloys.

It will be appreciated that various methods of attachment of the membrane may be utilized to practice the teachings of the present invention. It will be further appreciated by those skilled in the art, the membrane 30 may extend from a base portion 54 or top portion 56 of the outer wall 24 to create a single upper or lower tray. In one presently preferred embodiment, the membrane 30 is integral with, and preferably formed of the same material, as the arcuate members 12, 18.

Preferably, the first and second arcuate members 12, 18 are configured such that a portion 38 of the frame member 26 of the first arcuate member 12 can be positioned to closely overlap a portion 40 of the frame member 26 of the second arcuate member 18, thereby forming an overlap portion 42. The first and second arcuate members 12, 18 may be configured such that the first and second arcuate members 12, 18 may be positioned relative to each other in such a manner so as to form a substantially U-shaped channel 46 disposed between the outer walls 24 of the first and second arcuate members 12, 18 and a perimeter 48 of the overlap portion 42 of the frame member 26. It will be appreciated by those skilled in the art that the channel 46, may preferably approximate the curvature of the dentition of a patient. Accordingly, each arcuate member 12, 18 is adapted to receive a quantity of impression material (not shown) within the channel 46.

In one presently preferred embodiment, a handle 50 is attached to at least one of the arcuate members 12, 18. The handle 50 helps facilitate removal of the dental impression tray 10 without deforming the impression material introduced within the channel 46 of the tray 10. In the embodiment illustrated in FIGS. 1 through 4b and 7, the handle 50 is attached to and integral with the first arcuate member 12. It will be appreciated by those skilled in the art that there are various ways to configure a handle 50 or means to facilitate the introduction and removal of the dental impression tray 10 from a patients mouth. For example, some alternative forms may include, by way of illustration and not by limitation, tabs, grips or flange members formed or attached at various positions along the length of the arcuate members 12, 18.

With reference to FIGS. 1 and 2, at least one of the arcuate members 12, 18 includes a locking member 64 for retaining the impression material. In one presently preferred embodiment of the present invention, the locking member 64 includes an L-shaped flange member 66 which extends from the inside of the outer wall 24 along the length of each of the arcuate members 12, 18 selectively arranged on opposite sides of the membrane 30. It will be appreciated by those skilled in the art that where the membrane 30 extends from either the base portion 54 or the top portion 56 of the outer wall 26, the L-shaped locking member 66 is needed on only an interior of channel 46 of the dental impression tray 10.

With specific reference to FIG. 2, one arm 68 of the locking member or L-shaped flange 66 formed on each side of the membrane 30 extends toward the membrane 30. In this configuration, the impression material will fill into at least a portion of a groove 70 created by the L-shaped flange 66 when a patient bites down on the adjustable dental impression tray 10 as a dental mold is created. Those with skill in the art will appreciate that the L-shape flange 66 will generally secure the impression material to the adjustable dental impression tray 10 as it is removed from the mouth of a patient.

In another presently preferred embodiment of the present invention, the locking member 64 may include receiving apertures or vents 272 (see FIG. 7) configured within the length of at least one of the arcuate members 12, 18 which allows a portion of the impression material (not shown) to flow through the receiving apertures or vents 272 and, accordingly, sufficiently anchor itself to the arcuate member 12, 18. It will be appreciated by those skilled in the art that the teachings of this invention may be practiced using a variety of configurations of locking members 64.

Figure 3:
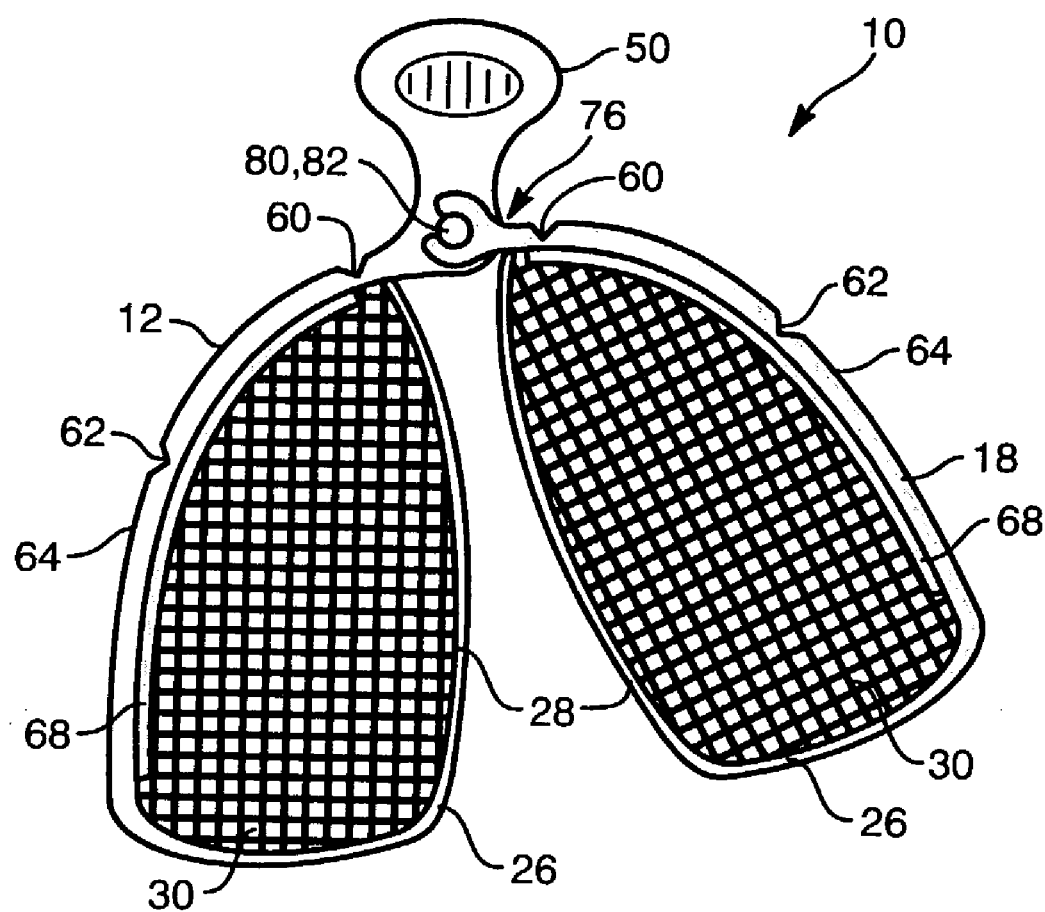
FIG. 3 is a top plan view of the embodiment of FIG. 1 with a first and second arcuate member adjusted into an open position.
Figure 4A:
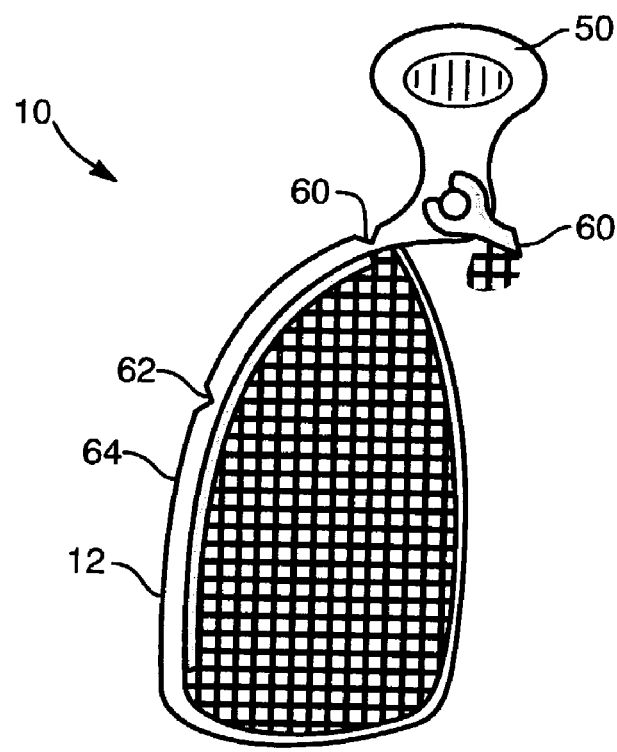
FIG. 4a is a top plan view of the embodiment of FIG. 1 showing an arcuate member broken away to form a quadrant tray.
Figure 4B:
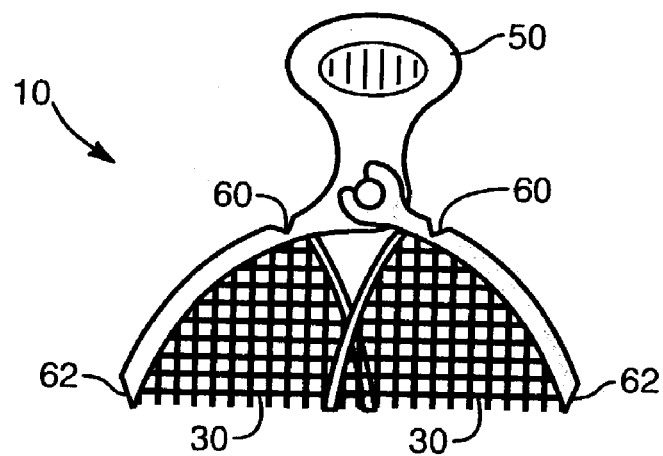
FIG. 4b is a top plan view of the embodiment of FIG. 1 showing an both arcuate members partially broken away to form an anterior tray.

Referring now to FIGS. 3, 4a and 4b, the outer wall 24 of at least one of the arcuate members 12, 18 may include a proximal notch 60 adjacent the proximal ends 16, 22 of each arcuate member 12, 18 which permits the user to break the length of the arcuate member 12, 18 at the proximal notch 60, if desired. It will be appreciated by those skilled in the art that this allows the user to create a "quadrant" dental tray for taking an impression of the left or right portions of the patient's upper or lower dentition, as best illustrated in FIG. 4a. The outer wall 24 of the arcuate members 12, 18 may also include a second notch 62 formed in the length of the arcuate members 12, 18 between the distal 14, 20 and proximal ends 16, 22 thereof, which permits the user to break the length of the arcuate members 12, 18 at the notches 62, if desired. It will be appreciated by those skilled in the art that breaking the arcuate members 12, 18 at the notch 62, respectively, allows the user to create an "anterior" dental tray for taking a dental impression of the front portion of the upper or lower dentition of a patient, as best illustrated in FIG. 4b.

It will be further appreciated by those skilled in the art that the first and second arcuate members 12, 18 must be formed of sufficient rigidity to allow a user to break the length of the arcuate members 12, 18 at the notches 60, 62 without deforming the remaining length of the arcuate members. It will also be appreciated that the depth of the notches 60, 62 may vary depending on the material used to create the arcuate members 12, 18. Additionally, it will be appreciated by those skilled in the art that there are numerous ways to allow a user to break the length of the arcuate members 12, 18 in such a manner so to form a "quadrant" or "anterior" impression tray, which are intended to fall within the teachings of present invention.

Figure 5:
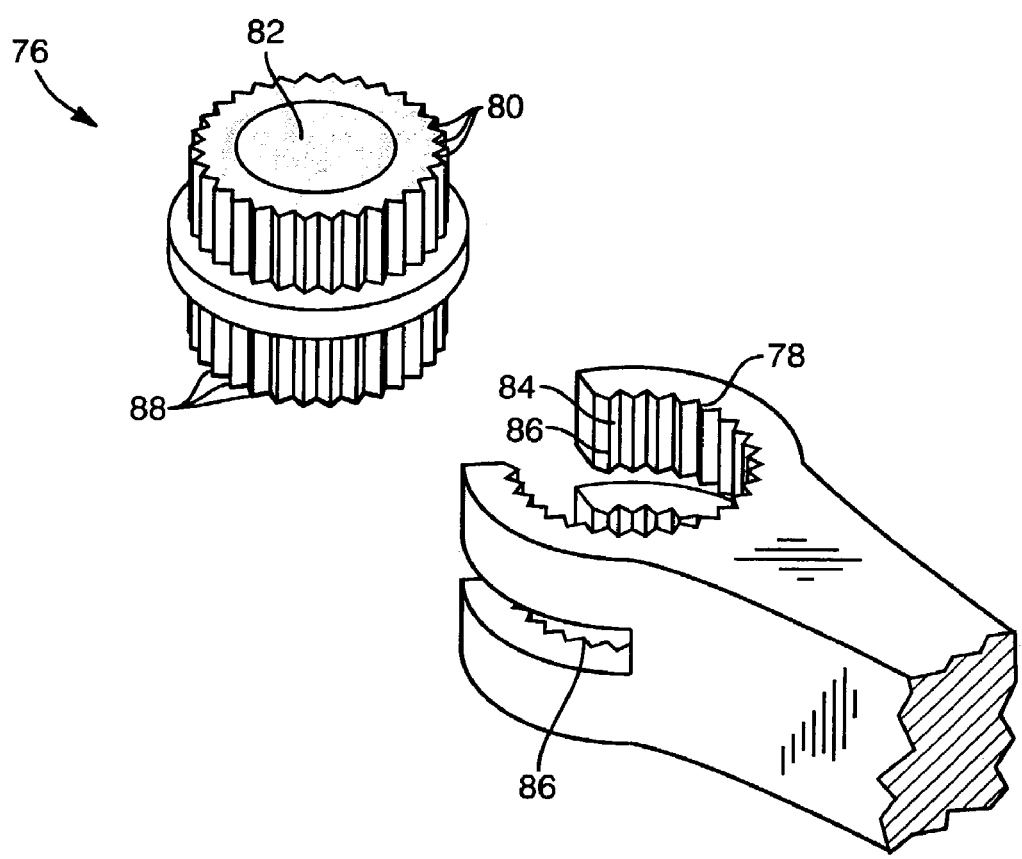
FIG. 5 is a perspective exploded view of the embodiment of FIG. 1 showing an adjustment mechanism.

Referring now to FIGS. 3 and 5, one presently preferred embodiment of the adjustable dental impression tray 10 of the present invention preferably includes an adjustment mechanism 76 for selectively adjusting the position of the first arcuate member 12 relative to the second arcuate member 18. In one preferred embodiment, the adjustment mechanism 76 may include an opening 78 configured within the proximal end 22 of the second arcuate member 18 and a fastener member 80, corresponding to the opening 78 in the second arcuate member 18, configured within the proximal end 16 first arcuate member 12. The fastener member 80 may include a post or shaft 82 configured within the proximal end 16 of the first arcuate member 12, with the opening 78 generally configured in the shape of a "C." An interior surface 84 of the opening 78 may be configured with teeth members 86 and the post or shaft 82 may be configured with corresponding teeth 88 such that the opening 78 and post or shaft 82 may be positioned in a movable, mating engagement respective to each other.

A first prong or section 90 and a second prong or section 92 of the C-shaped opening 78 are preferably flexible in structure, thereby allowing the user to apply a sufficient force to the second arcuate member 18 such that the first prong 90 and the second prong 92 spread apart so as to allow the second arcuate member 18 to rotate about the post or shaft 82 of the first arcuate member 12. In this configuration, the first and second arcuate members 12, 18 may be selectively positioned relative to each other. It will be appreciated by those skilled in the art that the first and second prongs or sections 90, 92 of the opening 78 should be of such rigidity that when the width of the adjustable dental impression tray 110 is adjusted, the C-shaped opening 78 returns to mating engagement with the post or shaft 82, thereby selectively retaining the first and second arcuate members 12, 18 in a fixed position relative to each other. The configuration of the opening 78 (and, subsequently, the first and second prongs 980, 92) will thus be based in part upon the material forming the arcuate members 12, 18.

Other adjustment mechanisms may include, by way of illustration and not by limitation, various fasteners attached to the first and second arcuate members 12, 18 including, by way of illustration only and not by limitation, "ball cap" fasteners, ratchet strap fasteners or other similar types of conventional fasteners.

Figure 6:
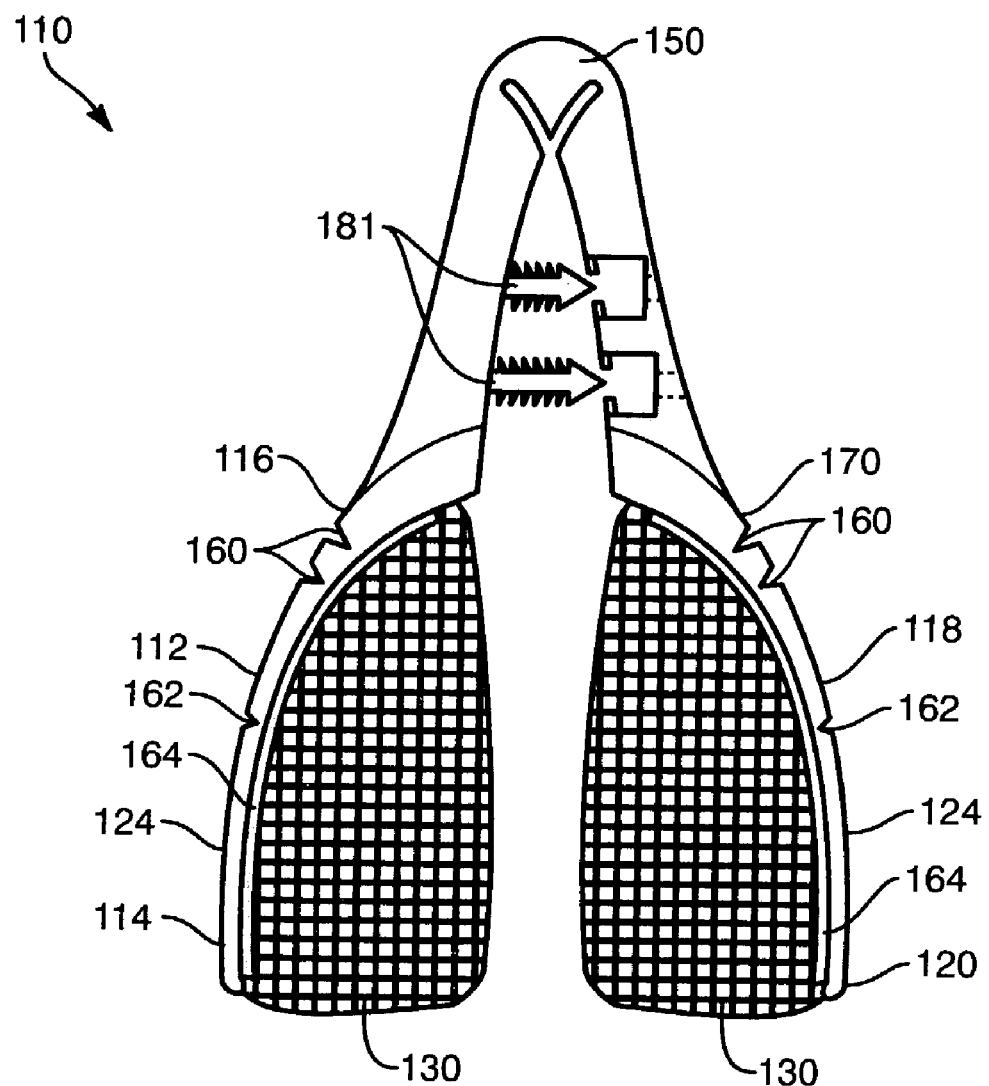
FIG. 6 is a top plan view of yet another embodiment of the present invention illustrating an alternative adjustment mechanism.

Turning now to FIG. 6, an alternative presently preferred embodiment of the adjustable dental impression tray is generally designated at 110. In this embodiment, a first arcuate member 112, having a distal end 114 and a proximal end 116, is connected to and integral with a second arcuate member 118 having a distal end 120 and a proximal end 122, at the proximal ends 116, 122 of the arcuate members 112, 118. As with previously described embodiments, a membrane 130 may extend from an outer wall 124 of each arcuate member 112, 118 along the length of the outer wall 124. The membrane 130 in this embodiment extends from a centerline portion (not shown) of the outer wall 24, but could also extend from a base or top portion (not shown), if desired.

As in earlier embodiments, the first and second arcuate members 112, 118 are configured to overlap and form a substantially U-shaped channel which approximates the curvature of the dentition of a patient. Accordingly, each arcuate member 112, 118 is adapted to receive within the channel a quantity of impression material (not shown). A handle 150 portion may be configured adjacent the proximal ends 116, 122 of one or more of the arcuate member 112, 118. As in the embodiments described above, each arcuate member 112, 118 may include a locking member 164 for retaining the impression material within the channel. The embodiment shown in FIG. 6 may also include one or more proximal notches 160 formed at the proximal ends 116, 122 of the arcuate members 112, 118 and one or more medial notches 162 formed in the length of the arcuate members 112, 118 between the distal 114, 120 and proximal ends 116, 122 thereof. These notches 160, 162 allow the user to break the length of the arcuate members 112, 118 of the adjustable dental impression tray 110 at the specified notches 160, 162 to create a "quadrant" or "anterior" dental impression tray for taking an impression of the left or right portion of the upper or lower dentition of a patient, or the front portion of the upper or lower dentition of the patient, respectively.

The embodiment illustrated in FIG. 6 also includes an alternative embodiment of an adjustment mechanism 176. Preferably, the adjustment mechanism 176 may include at least one and preferably two ratchet strips 181 attached to the first arcuate member 112. At least one and preferably two corresponding openings 178 may be configured within the second arcuate member 118 opposite the ratchet strips 181. The opening 178 includes a neck portion 179 configured to receive and retain the ratchet strips 181, thus allowing the dental tray to be adjusted to a variety of positions. It will be appreciated by those skilled in the art that other embodiments may incorporate as an adjustment mechanism a wire being sufficiently rigid to hold the first and second arcuate members 112, 118 in a fixed position relative to each other and yet malleable enough to selectively reposition the first and second arcuate members 112, 118 relative to each other, as desired.

Figure 7:
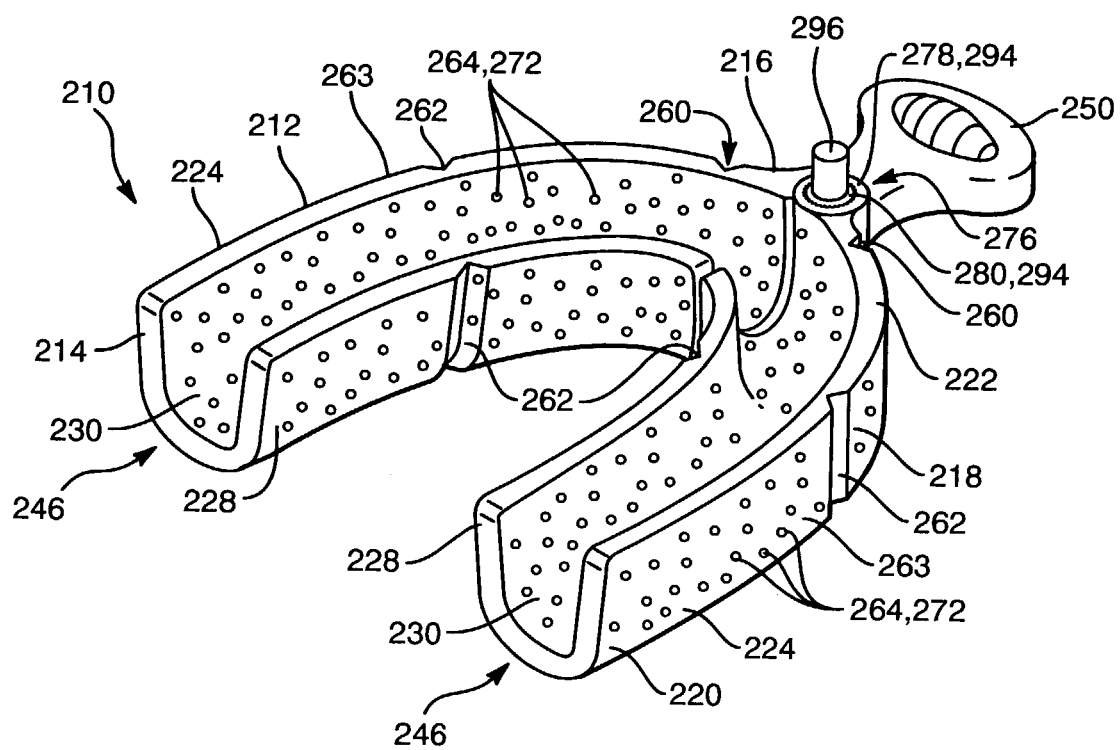
FIG. 7 is a perspective view of another embodiment of the present invention illustrating arcuate members with inner and outer walls.

Referring now to FIG. 7, another alternative presently preferred embodiment of the present invention is generally designated at 210. In this embodiment, a first arcuate member 212, having a distal end 214 and a proximal end 216, is engageably disposed in relation to a second arcuate member 218 having a distal end 220 and a proximal end 222. The first and second arcuate members 212, 218 each include an inner wall 228 spaced apart from an outer wall 224. A membrane 230 may extend between the inner wall 228 and the outer wall 224 thus forming a generally U-shaped channel 246 approximating the curvature of the dentition of a patient. In one presently preferred embodiment of the adjustable dental impression tray 210 shown in FIG. 7, the inner wall 228, outer wall 224, and the membrane 230, are formed as an integral unit relative to each other, thus being unitary in nature (i.e. monolithically formed as a single unit).

In the presently preferred embodiment illustrated in FIG. 7, a handle 250 is attached to at least one of the arcuate members 212, 218. As described in earlier embodiments, the handle 250 may be attached to and integral with the first arcuate member 212. As also described above, at least one of the arcuate members 212, 218 and preferably each arcuate member 212, 218 includes a locking member 264 for retaining impression material. In one presently preferred embodiment, the locking member 264 may includes receiving apertures or vents 272 formed within the length of at least one and preferably each of the arcuate members 212, 218. Preferably, the receiving apertures or vents 272 are formed within the inner wall 228, the outer wall 224, the membrane 230 or any combination thereof to provide sufficient anchoring contact points. In operation, the receiving apertures or vents 272 allow a portion of the impression material to flow through and anchor itself to at least a portion of the length of one or more of the arcuate members 212, 218.

The outer wall 224 and the inner wall 228 of each of the arcuate members 212, 218 may be formed having a first notch 260 formed at the proximal ends 216, 222 of the arcuate members 212, 218 which permits the user to break the length of one or both of the arcuate members 212, 218 at the proximal notch 260. The outer wall 224 and inner wall 228 of the arcuate members 212, 218 may also be formed with a second notch 262 formed in the length of the arcuate members 212, 218 between the distal 214, 220 and proximal ends 216, 222, which permits the user to break the length of one or both of the arcuate members 212, 218 at these notches 262. It will be appreciated by those skilled in the art that the notches 260, 262 allow the user to create a "quadrant" dental tray for taking an impression of the left or right portions of the upper or lower dentition of a patient or an "anterior" dental tray for taking a dental impression of the front portion of the upper or lower dentition of a patient, respectively.

The presently preferred embodiment of the dental impression tray 210 of the present invention, as illustrated in FIG. 7, preferably includes an adjustment mechanism 276 for selectively adjusting the position of the first arcuate member 212 relative to the second arcuate member 218, thereby facilitating and adjustment in the width of the impression tray. The adjustment mechanism 276 preferably includes an opening 278 configured within the proximal end 222 of the second arcuate member 218 and a fastener member 280, corresponding to the opening 278, configured within the proximal end 216 of the first arcuate member 212. The fastener member 280 may include a first gear 294 configured within the proximal end 216 of the first arcuate member 212. The opening 278 may also be configured in gear formation about the first gear 294 to form concentric gears. A spring-loaded button 296, which when depressed, allows the concentric gears 294 to disengage thereby allowing the first and second arcuate members 212, 218 to rotate or move relative to each other. When the biased button 296 s released, the concentric gears 294 realign to hold the position of the first arcuate member 212 fixed relative to the second arcuate member 218.

Figure 8:
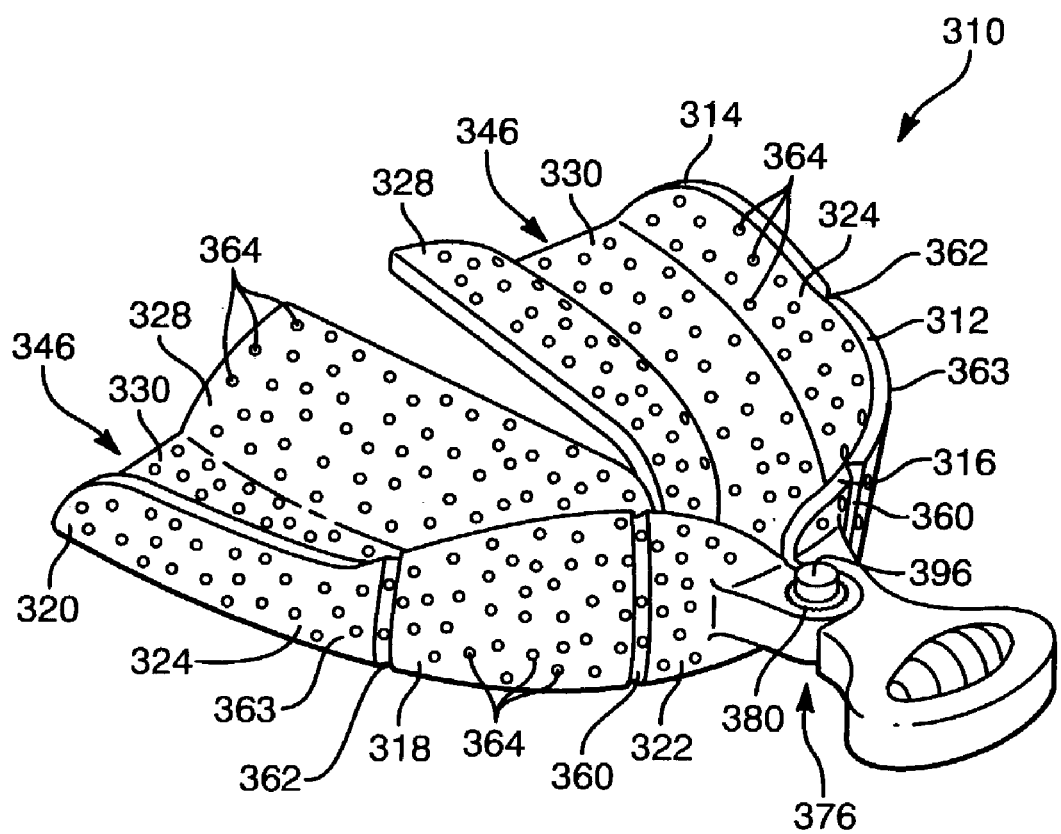
FIG. 8 is a perspective view of another embodiment of the present invention illustrating an upper tray with a palate support.

Referring now to FIG. 8, another alternative embodiment of the present invention is generally designated at 310. In this embodiment, a first arcuate member 312, having a distal end 314 and a proximal end 316, is connected to a second arcuate member 318 having a distal end 320 and a proximal end 322. As with previous embodiments, the first and second arcuate members 312, 318 each include an inner wall 328 spaced apart from an outer wall 324 and a membrane 330 extending between the inner wall 328 and the outer wall 324 to form a generally U-shaped channel approximating the curvature of the dentition of a patient. It will be appreciated by those skilled in the art that the embodiment illustrated in FIG. 8 may be used as an upper partial edentulous tray. Moreover, the teachings of the present invention may also be practiced on a variety of dental impression trays including, by way of illustration and not be limitation, full edentulous, triple bite and denture.

The adjustable dental impression tray 310 preferably includes a handle 350 attached to one or both of the arcuate members 312, 318 and a locking member 364 for retaining the impression material introduced into the channel 346. In one presently preferred embodiment of the present invention, the outer wall 324 and inner wall 328 of each of the arcuate members 312, 318 may include a first notch 360 formed at one or both of the proximal ends 316, 322 of the arcuate members 312, 318 and a second notch 362 formed between the distal 314, 320 and proximal ends 316, 322 thereof. These notches 360, 362 permit the user to break the length of the arcuate members 312, 318 to create a "quadrant" dental tray or an "anterior" dental tray, respectively, as desired.

In addition, the adjustable dental impression tray 310 preferably includes an adjustment mechanism 376 for selectively adjusting the position of the first arcuate member 312 relative to the second arcuate member 318. The adjustment mechanism 376 may include a post member 396 and a fastener member 380 configured to matingly engage the post member 396. In one preferred embodiment, the first and second arcuate members 312, 318 are positioned relative to each other and permanently snapped together to approximate the dentition of a patient. It will be appreciated by those skilled in the art that any number of snap members or fasteners may be utilized to selectively dispose the first arcuate member 312 to one or more preselected positions relative to the second arcuate member 318.

Referring now to FIGS. 9-13, another alternative preferred embodiment of an adjustable dental impression tray 410, in accordance with the present invention, may include a first arcuate member 412 having a distal end 414 and a proximal end 416 defining a longitudinal direction 411a. A second arcuate member 418, having a distal end 420 and a proximal end 422, may movably connect to the first arcuate member 412 adjacent the proximal ends 416, 422 of each of the arcuate members 412, 418, respectively. The arcuate members 412, 418 may be connected so as to form a region of limited symmetry 423 about an axis 425 extending in substantially the longitudinal direction 411a. A plane extending in a transverse direction 411c and the longitudinal direction 411a may substantially symmetrically divide the region of limited symmetry 425. A transverse direction 411c may be defined as being orthogonal to both the longitudinal and lateral directions 411a, 411b.

In one presently preferred embodiment of the present invention, the first and second arcuate members 412, 418 may each include an outer wall 424 extending in a transverse direction 411c away from a platform surface 430. A portion of a platform surface 430a may be configured as part of the first arcuate member 412. Another portion of a platform surface 430b may be configured as part of the second arcuate member 418. The platform surfaces 430 of the first and second accurate member 412, 418 may extend in both the longitudinal and lateral directions 411a, 411b in a manner suitable for supporting moldable impression material.

If desired, an inner wall 428 may also extend in a transverse direction 411c away from the platform surface 430. A height 429 of the inner wall 428 may be selected to assist in focusing and urging the impression material against the inside of the dentition of a patient.

In one presently preferred embodiment, the first and second arcuate members 412, 418 may be configured such that a portion 438 of the first arcuate member 412 may be positioned to overlap a portion 440 of the second arcuate member 418, thereby forming an overlap portion 442. The first and second arcuate members 412, 418 may be configured such that they may be positioned relative to each other to form a substantially U-shaped channel 446 formed between the outer walls 424. It will be appreciated by those skilled in the art that this channel 446 may preferably approximate the curvature of the dentition of a patient. Accordingly, each arcuate member 412, 418 is adapted to receive a quantity of impression material (not shown) within the channel 446 as defined by the outer wall 424 and the inner wall 428 of each of the arcuate members 412, 418.

In selected embodiments, a handle 450 may be attached to at least one of the arcuate members 412, 418. The handle 450 provides means to facilitate the introduction and removal of the dental impression tray 410 into and from the mouth of a patient without deforming the impression material there within. It will be appreciated by those skilled in the art that there are various ways to configure the handle 450 or other conventional means or methods to facilitate the introduction and removal of the dental impression tray 410. Some alternative forms may include for example, but not by way of limitation, tabs, grips or flange members attached at various positions along the length of the arcuate members 412, 418.

In one presently preferred embodiment of the present invention, receiving apertures or vents 452 may be formed within at least one of the arcuate members 12, 18 to promote adhesion of the impression material introduced into the channel 446. That is, the receiving apertures or vents 452 permit the impression material to flow therethrough. Upon curing, the resulting adhesion promotes removal (from the patient's mouth) of the impression material in conjunction with the dental impression tray 410. Preferably, receiving apertures or vents 452 may be formed in the outer walls 424, the inner walls 428, the platform surface 430 or any combination thereof in relation to the length of the arcuate members 412, 418.

One or both of the arcuate members 412, 418 may include a first notch or weakened region 460 formed at the proximal ends 416, 422 thereof, thus permitting a user to break and remove a portion of the length of the accurate member 412, 418 of the dental impression tray 410 to conform the tray to the task at hand. The first or proximal notch 460 allows the user to create a "quadrant" dental tray for taking an impression of the left or right portions of the dentition of a patient. The arcuate members 412, 418 may also include a second notch or weakened region 462 formed in the length of one or both of the arcuate members 412, 418 between the distal end 414, 420 and proximal end 416, 422, respectively, thereby permitting a user to similarly break the length of the arcuate member 412, 418 of the impression tray 410. A break in the arcuate member 412, 418 at the second or medial notch 462 thus allows the user to create an "anterior" dental tray for taking a dental impression of the front portion of the upper or lower dentition of a patient.

The first and second arcuate members 412, 418 may be selected to have sufficient rigidity to allow a user to break the length of the arcuate members 412, 418 at the notches or weakened areas 460, 462 without affecting the overall structural integrity of the adjustable dental impression tray 410. As will be appreciated, the depth or score of the notches 460, 462 formed in the length of one or both of the arcuate members 412, 418 may vary depending on the material comprising the dental impression tray 410. Preferably, the arcuate members 412, 418 may be formed in any manner to provide controlled breaking and removal of the notched sections from the length of the arcuate members 412, 418. Additional weakened or scored regions 464 extending in substantially a longitudinal direction along the outer walls 424 may be incorporated into the structural design of the dental impression tray, if desired, to provide an efficient means for adjusting the height thereof.

A dental impression tray 410, in accordance with one presently preferred embodiment of the present invention, may include a pivot 474 to facilitate selective rotational movement between the first and second arcuate members 412, 418, thereby adjusting the dimensional width of the channel 446 and affecting the size of the impression tray, as desired. An adjustment mechanism 476 may selectively adjust and retain the position of the first arcuate member 412 relative to the second arcuate member 418. As will be appreciated by those skilled in the art, the adjustment mechanism 476 may be formed having any suitable configuration or structural design sufficient to accommodate the teachings of the present invention. For example, in certain embodiments of the present invention, the adjustment mechanism 476 may include a receiving aperture 478 configured at the proximal end 422 of the second arcuate member 418. A stud or locking pin 480, corresponding to the receiving aperture 478 of the second arcuate member 418, may be configured as part of the proximal end 416 of the first arcuate member 412. When the stud or locking pin 480 engages the receiving aperture 478, two securement points (the other being the pivot 474) are preferably provided, and the position of the first and second arcuate members 412, 418 may be substantially fixed with respect to one another.

In one presently preferred embodiment, the second arcuate member 418 may include several receiving apertures 478 (i.e., small, medium, large and extra large) to provide multiple, possible adjustment positions 482a, 482b, 482c, 482d, as best illustrated in FIGS. 10-13. These adjustment positions 482 may be selected to correspond to common sizes and configurations of the mouth of patients. The number and increment of the fixed adjustment positions 482 and the resulting spacing between the first and second arcuate members 412, 418 may be selected fit a complete range of mouth sizes and configurations (i.e., small, medium, large and extra large), consistent with the selected adjustment in the dimensional width of the channel 446 receiving the impression material (not shown) and dentition of the patient.

Figure 9:
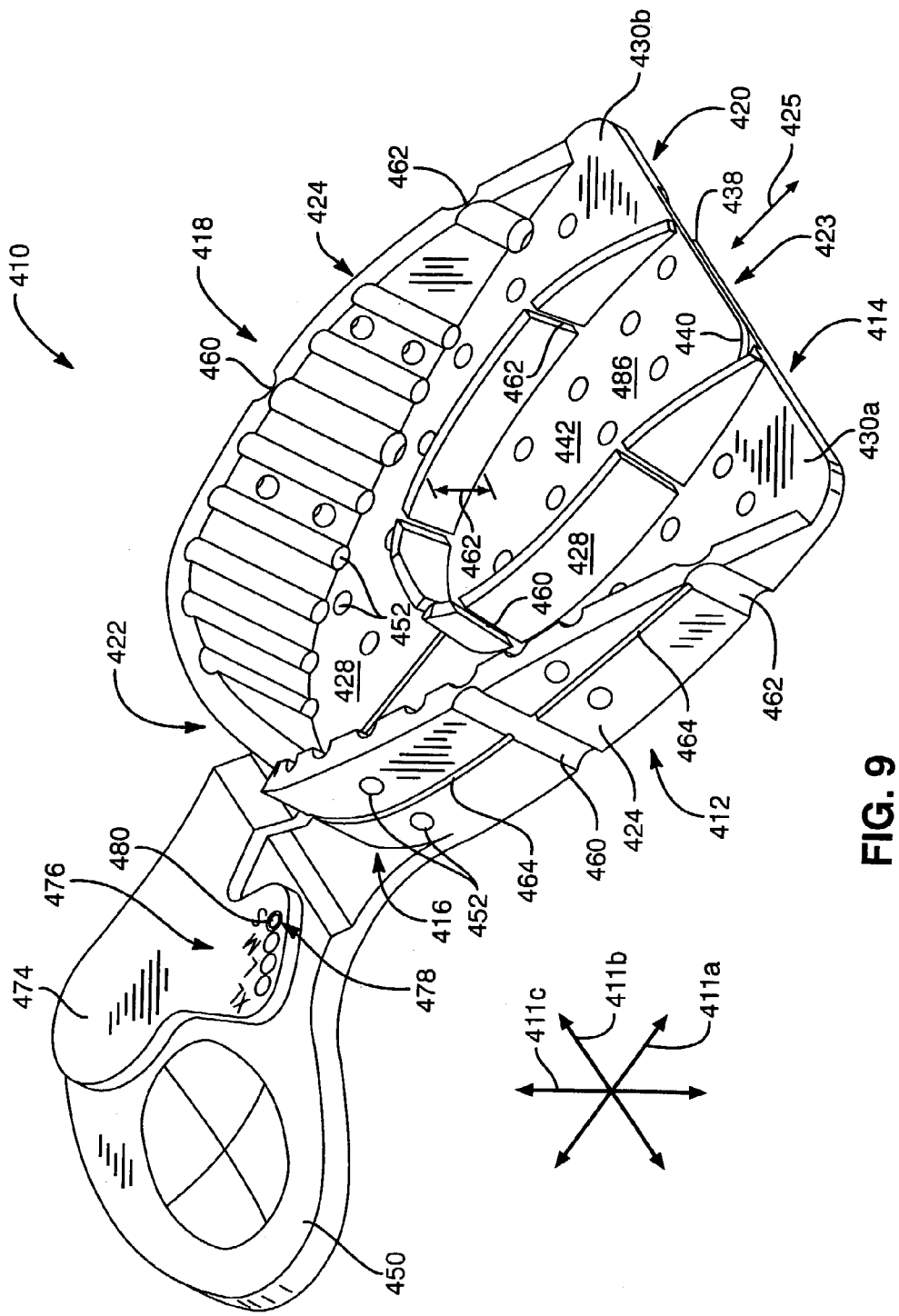
FIG. 9 is a perspective view of yet another presently preferred embodiment of an adjustable dental impression tray in accordance with the present invention.
Figure 10:
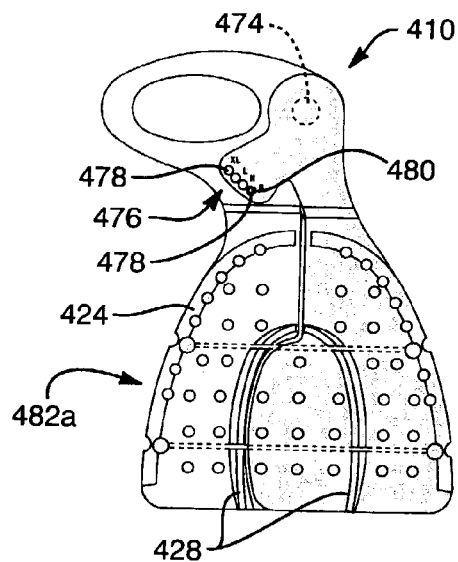
FIG. 10 is a top plan view of the embodiment of FIG. 9 showing the impression tray selectively disposed in a first position (e.g., a "small" position) in accordance with the adjustability of the present invention.
Figure 11:
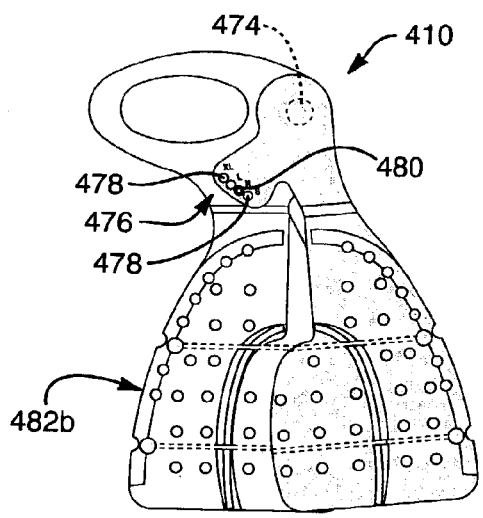
FIG. 11 is a top plan view of the embodiment of FIG. 9 showing the impression tray selectively disposed in a second position (e.g., a "medium" position) in accordance with the adjustability of the present invention.
Figure 12:
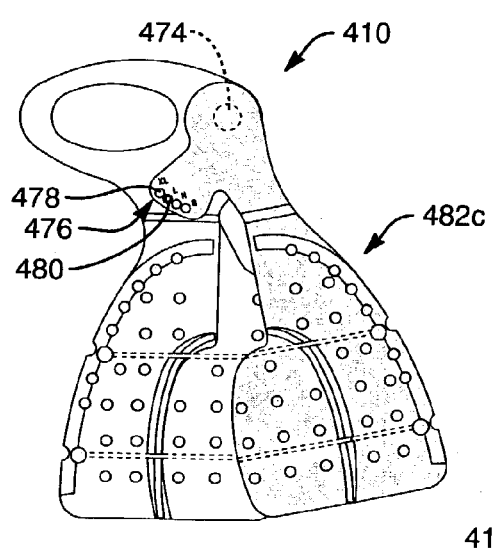
FIG. 12 is a top plan view of the embodiment of FIG. 9 showing the impression tray selectively disposed in a third position (e.g., a "large" position) in accordance with the adjustability of the present invention.
Figure 13:
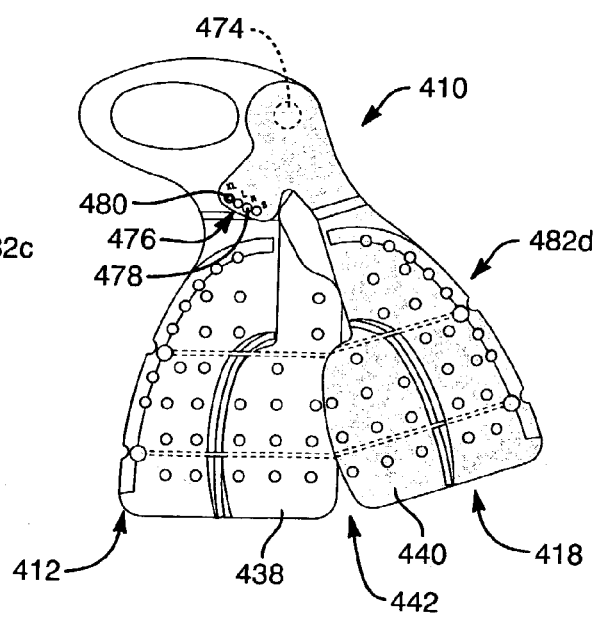
FIG. 13 is a top plan view of the embodiment of FIG. 9 showing the impression tray selectively disposed in a fourth position (e.g., an "extra large" position) in accordance with the adjustability of the present invention.
Figure 14:
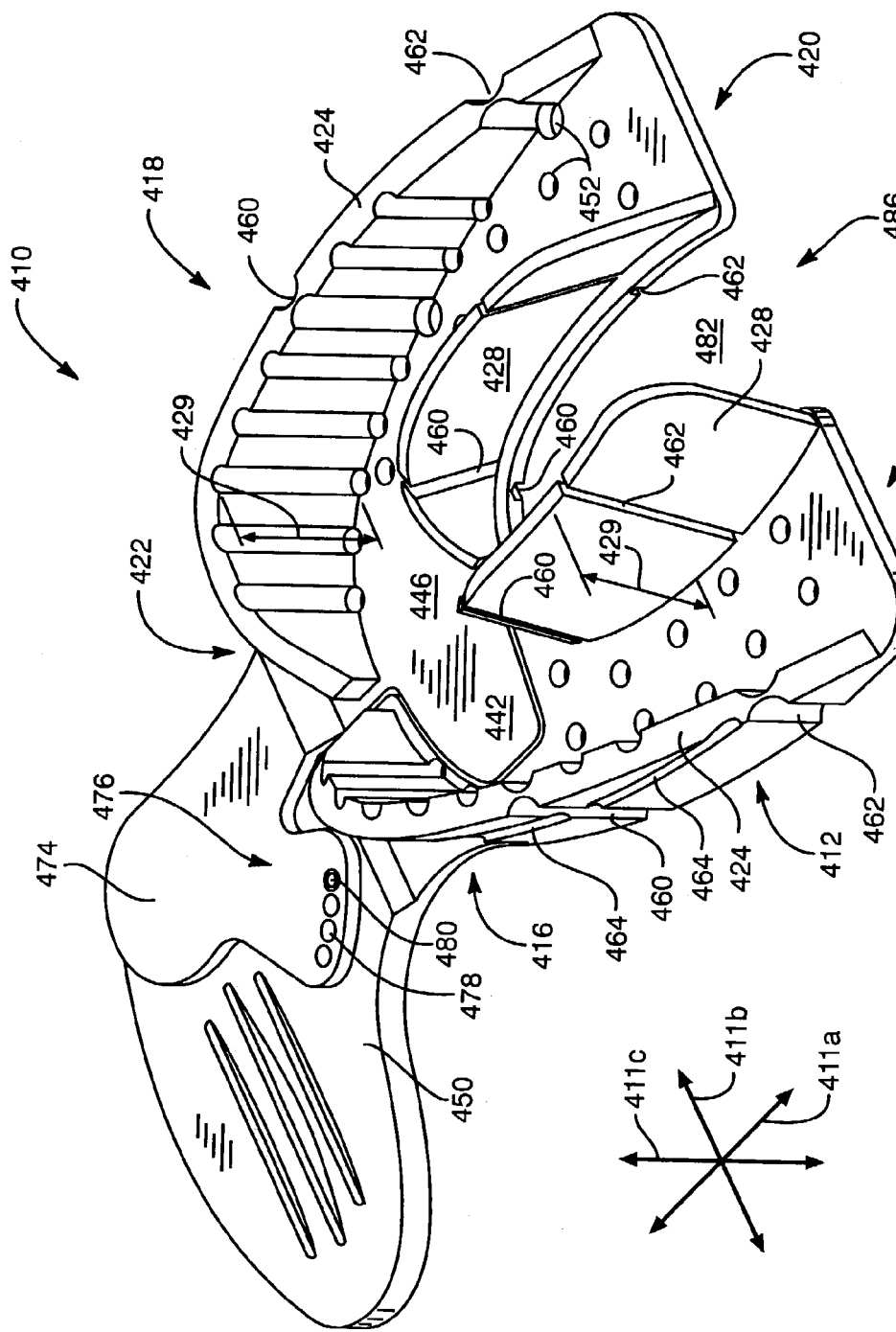
FIG. 14 is a perspective view of yet another presently preferred embodiment of an adjustable dental impression tray in accordance with the present invention.
Figure 15:
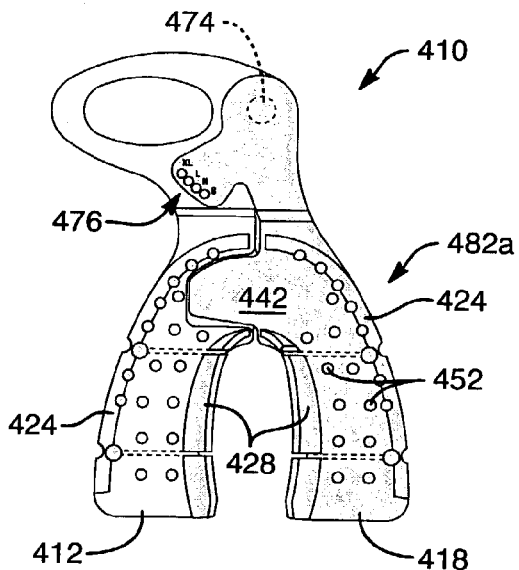
FIG. 15 is a top plan view of the embodiment of FIG. 14 showing the impression tray selectively disposed in a first position (e.g., a "small" position) in accordance with the adjustability of the present invention.
Figure 16:
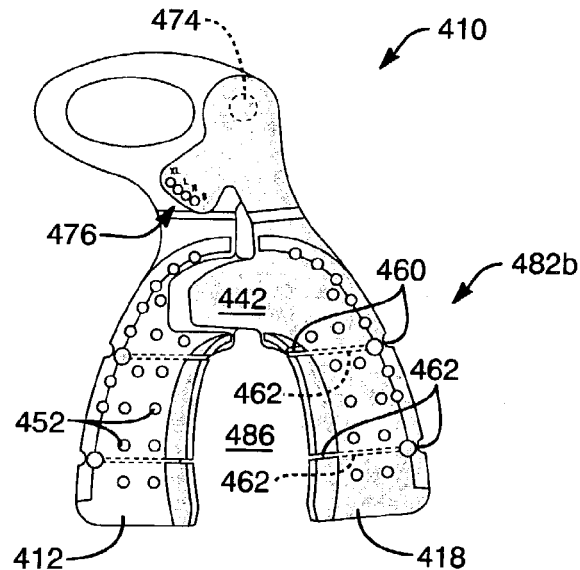
FIG. 16 is a top plan view of the embodiment of FIG. 14 showing the impression tray selectively disposed in a second position (e.g., a "medium" position) in accordance with the adjustability of the present invention.

In one presently preferred embodiment of the present invention, the dimensions and design of the adjustable dental impression tray 410 may be modified to provide an impression tray specifically designed to take impressions of the upper or lower dentition of the patient. For example, an impression tray 410 for taking an impression of the upper dentition in accordance with the present invention may include a platform surface 430a, 430b extending and overlapping in the region 486 between the inner walls 428, as best shown in FIG. 9. In selected applications, the platform surface 430 preferably supports impression material for taking an impression of the pallet of a patient.

Referring now to FIGS. 14-18, in consideration of other applications, a platform formed in the center region 486 may impede the use of the dental impression tray 410. For example, in taking an impression of the lower dentition of a patient, the tongue may need to be accommodated. An open center region 486 may allow the tongue to be positioned therein and pass therethrough, thus preventing the tongue from interfering with the impression process. Additionally, the shape, size, contour and the like of the outer and inner walls 424, 428 may be selected to complement the anatomical features of the upper dentition or lower dentition of the patient.

Figure 17:
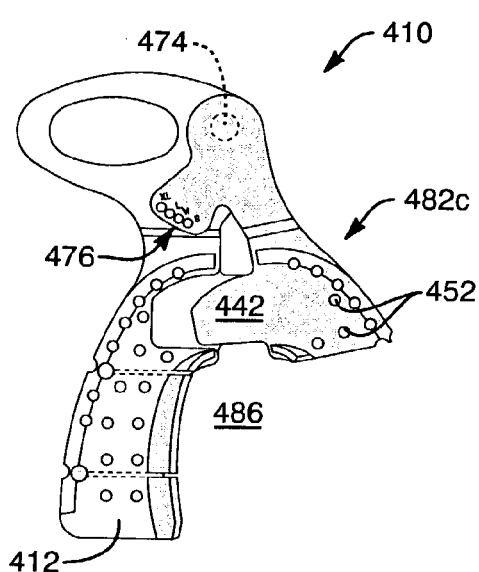
FIG. 17 is a top plan view of the embodiment of FIG. 14 showing the impression tray selectively disposed in a third position (e.g., a "large" position) with a portion of one of the arcuate members removed or broken away in accordance with one presently preferred embodiment of the present invention.
Figure 18:
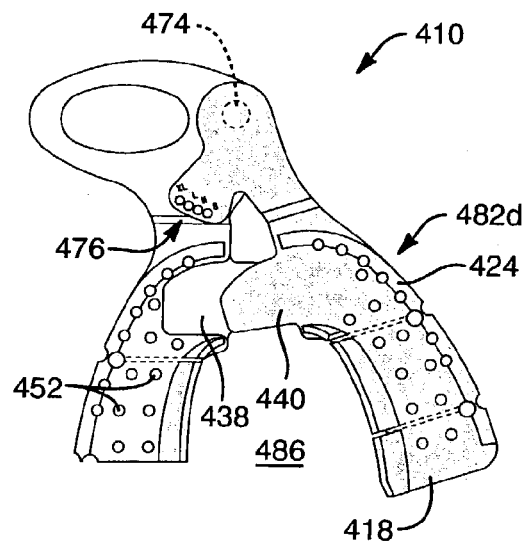
FIG. 18 is a top plan view of the embodiment of FIG. 14 showing the impression tray selectively disposed in a fourth position (e.g., an "extra large" position) with a portion of one of the arcuate members removed or broken away in accordance with one presently preferred embodiment of the present invention.

Referring now to FIGS. 17 and 18, as discussed hereinabove, the first and second arcuate members 412, 418 may have notches or weakened regions 460, 462, 464 formed within the length thereof to guide and control the fracture and removal thereof. The number and location of the scored notches or weakened regions 460, 462, 464 are preferably selected to provide fracture or breakage points resulting in useful configurations and designs of the dental impression tray thereby facilitating selected applications (e.g., taking anterior or quadrant impressions). Any combination of notches 460, 462, 464 may be broken in the length of the arcuate members 412, 418 to provide a suitable impression tray 410 configuration, as desired and contemplated herein.

Referring now to FIGS. 9-19, the overlapping portions 440, 442 of the platform surface 430 may be selected to provide a substantially continuous surface throughout the various fixed positions 482 of the impression tray 410. That is, as the arcuate members 412, 418 pivot with respect to one another, the overlapping portions 440, 442 extend across the area in the platform 430, thus eliminating the void that would otherwise be generated. In this fashion, the platform surface 430 may provide sufficient support for the impression material irrespective of the fixed position 482.

Figure 19:
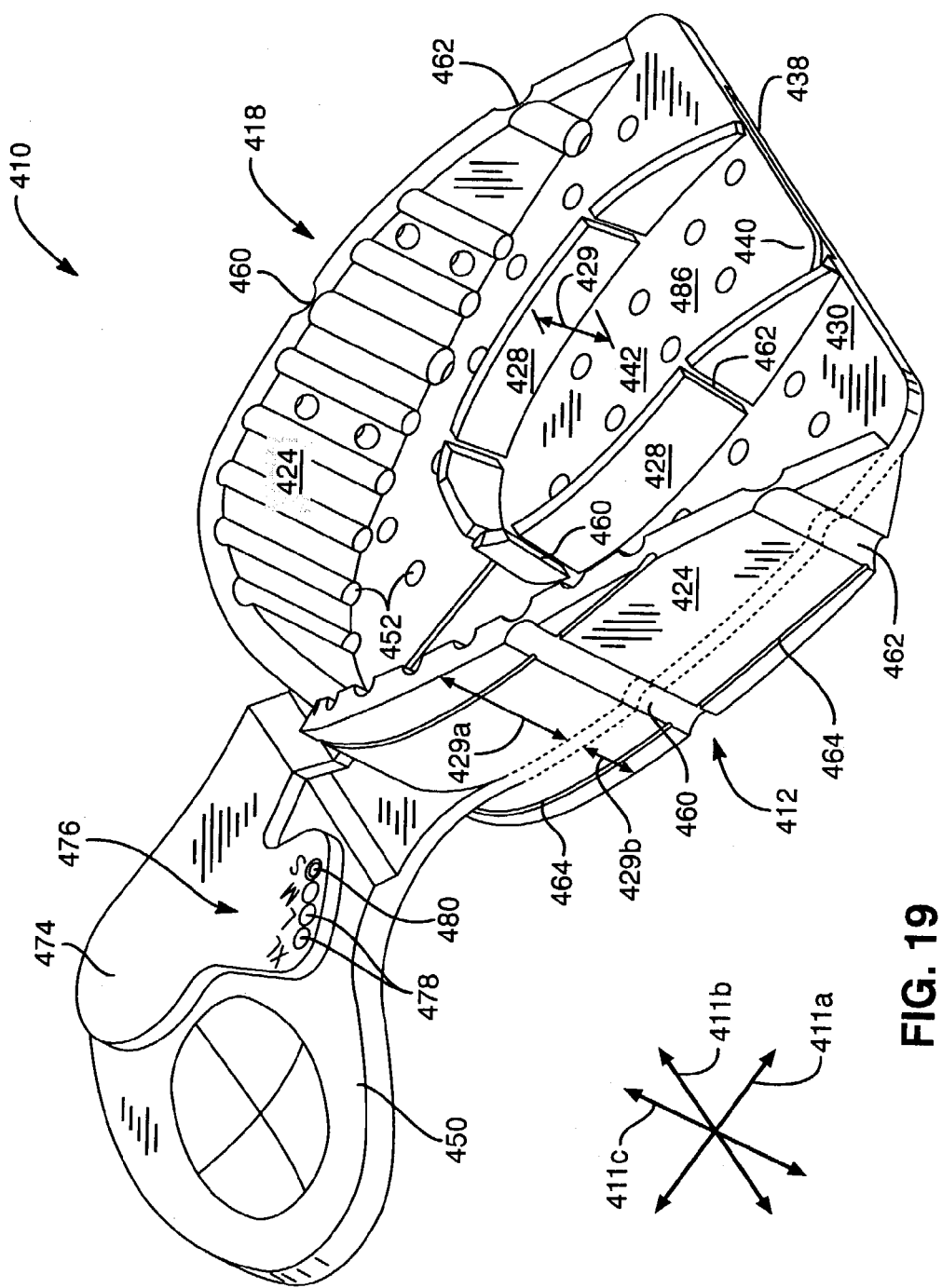
FIG. 19 is a perspective view of yet another presently preferred embodiment of an adjustable dental impression tray in accordance with the present invention.

Referring specifically to FIG. 19, an impression tray 410 in accordance with one presently preferred embodiment of the present invention may be adapted to simultaneously take impressions of the upper and lower dentition of a patient. Such an impression tray may be referred to as a "triple bite" or "multiple impression" tray to those of skill in the art.

In selected embodiments of a "triple bite" impression tray 410, in accordance with the present invention, the outer and inner walls 424, 428 may extend in both transverse directions 411c away from the platform surface 430. As appreciated, the extension on one side of the platform 430 need not be equal to the extension of the opposite side of the platform 430. The extension lengths 429a, 429b may be selected from a range sufficient to accommodate the anatomical differences of the upper and lower dentition of a patient. Additionally, the outer and inner walls 424, 428 may extend from the platform surface 430 at a length sufficient to form an acute angle therewith. That is, the walls 424, 428 do not have to be perpendicular to the platform surface 430, if desired.

As referenced hereinabove and illustrated in FIG. 19, receiving apertures or vents 452 may provide a mechanism to secure the impression material (not shown) within the channel 446 defined by the arcuate members 412, 418 of the adjustable dental impression tray 410, and assist in registering the impression of the upper dentition with the impression made from the lower dentition. Preferably, scored notches or weakened regions 460, 462 may be formed in a triple bite tray 410 to provide convenient breaking to form "quadrant" and "anterior" impression trays, respectively. Longitudinally extended scored notches or weakened regions 464 may also be incorporated into the structural design of the impression tray to provide convenient breaking to adjust or modify the height of the walls 424, 428 of the arcuate members 412, 418, if desired.

Referring again to FIGS. 1 through 19, the arcuate members of the embodiments in accordance with the present invention may each be injection molded using a plastic, polymer, composite, or the like. In certain embodiments high density polyethylene may be used. It will be appreciated by those of skill in the art, however, that the arcuate members may be formed of a variety of other sufficiently sturdy materials such as, metal alloys, fiberglass, ceramics, graphite, any of numerous organic, synthetic or processed materials, including thermoplastic or thermosetting polymers of high molecular weight with or without additives, such as, plasticisers, auto oxidants, extenders, colorants, ultraviolet light stabilizers, or fillers and/or other composite materials which are capable of being sterilized by conventional autoclave or chemical methods or processes. It will further be appreciated by those of skill in the art that the teachings of this invention may be practiced to create various styles of adjustable trays, including, upper and lower edentulous trays, upper and lower partial edentulous trays, upper and lower full trays, triple bite trays, and other types of impression trays.

The adjustable dental impression tray of the present invention may be used by approximating a patient's dentition and selectively positioning the first arcuate member relative to the second arcuate member to form a generally U-shaped channel which approximates the dentition. After comparing the approximation to the actual dentition and refining the position of the arcuate members relative to each other, impression material may be applied into the channel. The dental impression tray is inserted into the patient's mouth and onto the patient's dentition. After allowing the impression material to at least partially set, the dental impression tray is removed from patient's mouth. After utilizing the resulting mold for its intended purpose, the dental impression tray may be discarded.

In certain embodiments, scored notches or weakened regions may be formed in the arcuate members (e.g., formed in the outer walls inner walls, platform surface or any combination thereof) to provide multiple locations for adjusting the length of the arcuate members, and thus contouring the dental impression tray to be selectively adjusted to the application at hand in two dimensions (i.e., the width and length), as desired. This method of obtaining an impression may include the step of first approximating a patient's dentition and selectively positioning the first arcuate member relative to the second arcuate member such that a generally U-shaped channel approximates the dentition of the patient. The user may then determine which portion of the patient's dentition to create a mold for and break off the length of one of either of the first or second arcuate members at the appropriate notches to create a "quadrant" or an "anterior" tray. The impression material may then be introduced into the remaining channel of the dental impression tray. The adjustable dental impression tray may then be placed into the mouth of the patient in the area of the patient's dentition for which an impression is desired. After allowing the impression material to at least partially cure or set, the dental impression tray of the present invention may be removed from the mouth of the patient, thereby providing a workable impression of the targeted area of dentition.

From the above discussion, it will be appreciated that the present invention provides novel adjustable dental impression trays and methods for using the same. In particular, the present invention provides an adjustable dental impression tray which may be adjusted to accommodate various mouth sizes, bite radii of teeth, and to correspond to upper and/or lower, anterior or quadrant impression sites.

Unlike prior art devices, the present invention provides an adjustable dental impression tray comprising an adjustment assembly which may be manually adjusted to the specific size of the patient's mouth (e.g, small, medium, large or extra large), thereby eliminating the need for a dentist to inventory various conventional sizes of stock impression trays. Additionally, the present invention may be formed of a disposable material, thus avoiding the disadvantages associated with having to clean and sanitize metal impression trays.

Consistent with the foregoing, the present invention provides an adjustable dental impression tray which increases the accuracy of the impression cast, while decreasing dental chair time for the patient. Similarly, the present invention reduces the possibility of deformation of the impression cast, is simple in construction, effective in operation, and inexpensive to manufacture.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A dental impression tray, comprising:
   a first arcuate member comprising an engagement member and being jointlessly formed as a single unit with uniform composition throughout;
   a second arcuate member comprising an aperture, said second arcuate member being jointlessly formed as a single unit with uniform composition throughout;
   said engagement member of said first arcuate member directly engaging and retaining said aperture of said second arcuate member to provide pivoting of said first arcuate member with respect to said second arcuate member; and
   said first and second arcuate members forming a receiving channel of adjustable curvature.

2. The dental impression tray as defined in claim 1, wherein at least one of said first and second arcuate members comprises a handle.

3. The dental impression tray as defined in claim 2, wherein said engagement member comprises a post.

4. The dental impression tray as defined in claim 1, wherein at least one of said first and second arcuate members comprises a breakable notch formed along a length thereof.

5. The dental impression tray as defined in claim 1, wherein said first arcuate member comprises a platform comprising a length having an arcuate shape defining an outer edge and an inner edge and an outer wall extending generally perpendicularly from said platform proximate said outer edge.

6. The dental impression tray as defined in claim 5, wherein said second arcuate member comprises a platform comprising a length having an arcuate shape defining an outer edge and an inner edge and an outer wall extending generally perpendicularly from said platform proximate said outer edge.

7. The dental impression tray as defined in claim 6, wherein at least one of said first and second arcuate members comprises a breakable notch formed in said outer wall thereof.

8. The dental impression tray as defined in claim 6, wherein at least one of said first and second arcuate member comprises a breakable notch formed along said length of said platform.

9. The dental impression tray as defined in claim 1, wherein said receiving channel comprises a substantially U-shaped configuration approximating a curvature of the dentition of a patient.

10. The dental impression tray as defined in claim 1, wherein one of said first and second arcuate members comprises a locking member while the other comprises a plurality of receiving apertures positioned to periodically align and releasably engage said locking member at various stages of rotation of the first arcuate member with respect to the second arcuate member, wherein engagement of the locking member with each receiving aperture of the plurality of receiving apertures provides a registered position corresponding to a particular curvature.

11. A adjustable dental impression tray, comprising:
    a first arcuate member comprising an engagement member and being jointlessly formed as a single unit with uniform composition throughout;
    a second arcuate member jointlessly formed as a single unit with uniform composition throughout, said second arcuate member an aperture directly engaging and retaining said engagement member of said first arcuate member with respect to said second arcuate member;
    one of said first and second arcuate members further comprising an extension while the other comprises a plurality of receiving apertures, alignment between said extension and a first receiving aperture of said plurality of receiving apertures corresponding to a first relative positioning of said first and second arcuate members, alignment between said extension and a second receiving aperture of said plurality of receiving apertures corresponding to a second relative positioning of said first and second arcuate members, said second relative positioning being distinct from said first relative positioning; and
    at least one of said first and second arcuate members comprising at least one breakable notch formed along a length thereof.

12. The adjustable dental impression tray as defined in claim 11, wherein said aperture is open to surround only a portion of said engagement member.

13. The adjustable dental impression tray as defined in claim 11, wherein at least one of said first and second arcuate members comprises a handle.

14. The adjustable dental impression tray as defined in claim 11, wherein said first arcuate member comprises a platform comprising a length having an arcuate shape defining an outer edge and an inner edge and an outer wall extending generally perpendicularly from said platform proximate said outer edge.

15. The adjustable dental impression tray as defined in claim 14, wherein said second arcuate member comprises a platform comprising a length having an arcuate shape defining an outer edge and an inner edge and an outer wall extending generally perpendicularly from said platform proximate said outer edge.

16. The adjustable dental impression tray as defined in claim 15, wherein at least one of said breakable notches is formed in said outer wall of at least one of said first and second arcuate members.

17. The adjustable dental impression fray as defined in claim 15, wherein at least one of said breakable notches is formed along said length of said platform of at least one of said first and second arcuate members.

18. A method of adjusting a dental impression tray to the curvature of a patient's dentition, said method comprising the steps of selecting a dental impression tray comprising a first arcuate member including an engagement member and being jointlessly formed as a single unit with uniform composition throughout and a second arcuate member jointlessly formed as a single unit with uniform composition throughout, said second arcuate member comprising an aperture, wherein said engagement member of said first arcuate member directly engages and retains said aperture of said second arcuate member to provide pivoting of said first arcuate member with respect to said second arcuate member, said first and second arcuate members forming an arcuate channel of adjustable curvature;

adjusting said curvature of said arcuate channel by pivoting said first arcuate member with respect to said second arcuate member until the curvature of the arcuate channel substantially matches the curvature of at least a portion of said patient's dentition;

inserting an impression material into said arcuate channel;

urging said impression material against at least a portion of said patient's dentition;

permitting said impression material to at least partially set and record a negative image of at least a portion of said patient's dentition; and removing said dental impression tray from engagement with said portion of said patient's dentition.

19. The method as defined in claim 18, further comprising the step of discarding the dental impression tray.

20. The method as defined in claim 18, further comprising the step of adjusting the length of at least one arcuate member, wherein at least one of said first and second arcuate members comprises a breakable notch formed along a length thereof.

21. The method as defined in claim 20, further comprising the step of adjusting said length of at least one of said first and second arcuate members by breaking said breakable notch formed along the length thereof.

* * * * *

UNITED STATES PATENT AND TRADEMARK OFFICE
CERTIFICATE OF CORRECTION

PATENT NO.        : 7,270,540 B2
APPLICATION NO. : 10/427733
DATED             : September 18, 2007
INVENTOR(S)      : Gregory C. Skinner It is certified that error appears in the above-identified patent and that said Letters Patent is hereby corrected as shown below:

At column 18, line 38, after "member," please insert -- comprising --.

At column 18, line 40, after the first occurrence of the word "member," please insert -- to provide pivoting of said first arcuate member. --

At column 19, line 11, please delete "fray," and insert therefor -- tray --.

Signed and Sealed this

First Day of July, 2008

JON W. DUDAS
*Director of the United States Patent and Trademark Office*